United States Patent [19]
Primbsch

[11] 4,137,778
[45] Feb. 6, 1979

[54] METHOD AND APPARATUS FOR PRODUCING ULTRASONIC WAVES IN LIGHT ABSORBING SURFACES OF WORKPIECES

[75] Inventor: Erik Primbsch, Cologne, Fed. Rep. of Germany

[73] Assignee: Krautkramer-Branson, Incorporated, Stratford, Conn.

[21] Appl. No.: 839,167

[22] Filed: Oct. 4, 1977

[30] Foreign Application Priority Data

Mar. 5, 1977 [DE] Fed. Rep. of Germany ....... 2709725

[51] Int. Cl.$^2$ ............................................. G01N 29/00
[52] U.S. Cl. ......................................... 73/627; 73/643
[58] Field of Search .......................... 73/603, 627, 643; 134/1, 184

[56] References Cited

U.S. PATENT DOCUMENTS

| | | | |
|---|---|---|---|
| 3,503,804 | 3/1970 | Schneider | 134/1 |
| 3,978,713 | 9/1976 | Penney | 73/627 |

OTHER PUBLICATIONS

White, "Generation of Elastic Waves by Transient Surface Heating", Journal of Applied Physics, vol. 34, No. 12, pp. 3559–3567, Dec. 1963.

*Primary Examiner*—Stephen A. Kreitman
*Attorney, Agent, or Firm*—Ervin B. Steinberg; Philip J. Feig

[57] ABSTRACT

In order to stabilize the acoustic wave amplitude in a workpiece, where such acoustic wave is generated by a laser beam pulse transmitted upon the workpiece surface, laser pulses preceding the laser pulse used for acoustic evaluation are utilized to clean the workpiece surface from contamination. Cleaning of the workpiece surface to the bare metal provides a normalized surface condition in respect to absorbed pulsed laser beam energy and, hence, produces acoustic waves of substantially constant amplitude. Either the same laser producing the acoustic wave or a separate laser is used for vaporizing contamination at the workpiece surface where an acoustic wave is subsequently to be produced.

9 Claims, 2 Drawing Figures

METHOD AND APPARATUS FOR PRODUCING ULTRASONIC WAVES IN LIGHT ABSORBING SURFACES OF WORKPIECES

BRIEF SUMMARY OF THE INVENTION

This invention concerns a method and apparatus for producing ultrasonic waves resulting from thermal excitation in the light absorbing surface of a workpiece. More particularly, the invention concerns the production of an ultrasonic wave in the surface of a workpiece caused by the absorption of a laser beam pulse, and such ultrasonic wave being adapted for nondestructively testing such workpiece for internal defects.

The generation of acoustic waves responsive to sudden heating of a surface portion of a workpiece is well known, see "Werkstoffprufung mit Ultraschall" (book) J. & H. Krautkramer, 3rd edition, pages 148 to 149, Springer Verlag, Berlin/Heidelberg/New York (1975) and U.S. Pat. No. 3,978,713, dated Sept. 7, 1976 to C. M. Penney entitled "Laser Generation of Ultrasonic Waves for Nondestructive Testing".

The amplitude of the ultrasonic wave produced by thermal excitation is dependent upon the absorbed energy from the pulsed laser beam. The frequency spectrum of the acoustic wave is determined by the shape of the laser beam pulse. When performing nondestructive testing of workpieces with ultrasound, the thermal method of producing an acoustic wave is used when the acoustic energy cannot be imparted to the workpiece by a conventional coupling medium. For locating defects in the workpiece, the workpiece must be scanned by a finite acoustic beam propagated from the workpiece surface, the beam having generally a cross sectional area not exceeding a few square centimeters. When utilizing the contact-free generation of ultrasonic waves resulting from the thermal effect produced by a pulsed laser beam, different absorption characteristics prevailing along the surface of the workpiece lead to local variations of the sonic wave amplitude.

In practice, workpieces are contaminated unevenly along their surface. Cleaning of the surface, particularly when workpieces to be tested by the contact-free method are involved, is difficult if not impossible on account of the shortcomings inherent in such workpieces. Varying amplitudes of the acoustic wave due to different absorption of the laser energy complicate the quantitative evaluation of the test result since constant acoustic pressure generation from location to location is a prerequisite for such evaluation.

An object of this invention is the provision to assure the condition of constant laser pulse energy absorption from location to location when producing ultrasonic waves with laser beam energy and, thereby, providing constant acoustic wave amplitude along the entire workpiece surface.

In accordance with the invention disclosed hereafter, the problem pointed out heretofore is solved by providing for each laser energy responsive acoustic wave generation process, two or more coherent light pulses upon the workpiece surface portion at which the acoustic wave is to be generated. Only the acoustic wave caused by the last transmitted laser pulse is used for the ultrasonic test whereas the preceding transmitted laser beam pulses serve for eliminating surface contamination. In accordance with the invention, the known phenomenon that laser beam radiation can be utilized to vaporize a contaminant is employed.

It is apparent that clean metallic surfaces reflect more energy and, hence, absorb less energy than contaminated surfaces. The light energy absorbed by an oxidized or contaminated surface causes a localized heating and ultimately produces vaporization of the contaminant. It is advantageous that the contaminant layer generally has a lower thermal conductivity and a lower specific heat capacity than that of the base material. However, if in contrast clean metallic material is irradiated with pulsed laser beams of the same energy, no or only insignificant vaporization occurs since, on account of the higher reflectivity, a smaller amount of energy is absorbed. Moreover, by virtue of the higher thermal conductivity and higher specific heat capacity of the base material, a significantly lower degree of heating is obtained. It is not detrimental if the laser pulse energy is selected for removal of the most severe contamination, or layer of foreign substance, since the material erosion becomes self-limiting as soon as the clean surface presents itself.

The present method and several embodiments thereof will be more clearly apparent from the following description when taken in conjunction with the accompanying drawings.

DETAILED DESCRIPTION OF THE INVENTION

The method forming the present invention can be understood most clearly from the following example. A workpiece having a partially oxidized surface is to be tested by ultrasonic energy without establishing physical contact. The generation of a sonic energy pulse is accomplished by means of a laser beam pulse and reception of sonic energy is to be made, for instance, with a known transit time interferometer arrangement not forming a part of the present invention. The sonic waves are to be produced by means of a laser beam pulse of about 30 nanoseconds duration. The variations in sound pressure amplitude arising from the thermal sound generation in the oxidized region and in the clean metallic region of the workpiece surface have an adverse effect on the test result. As an example, the sound pressure amplitude in the oxidized region is 20 db greater than that in the clean workpiece surface region.

Figure 1:
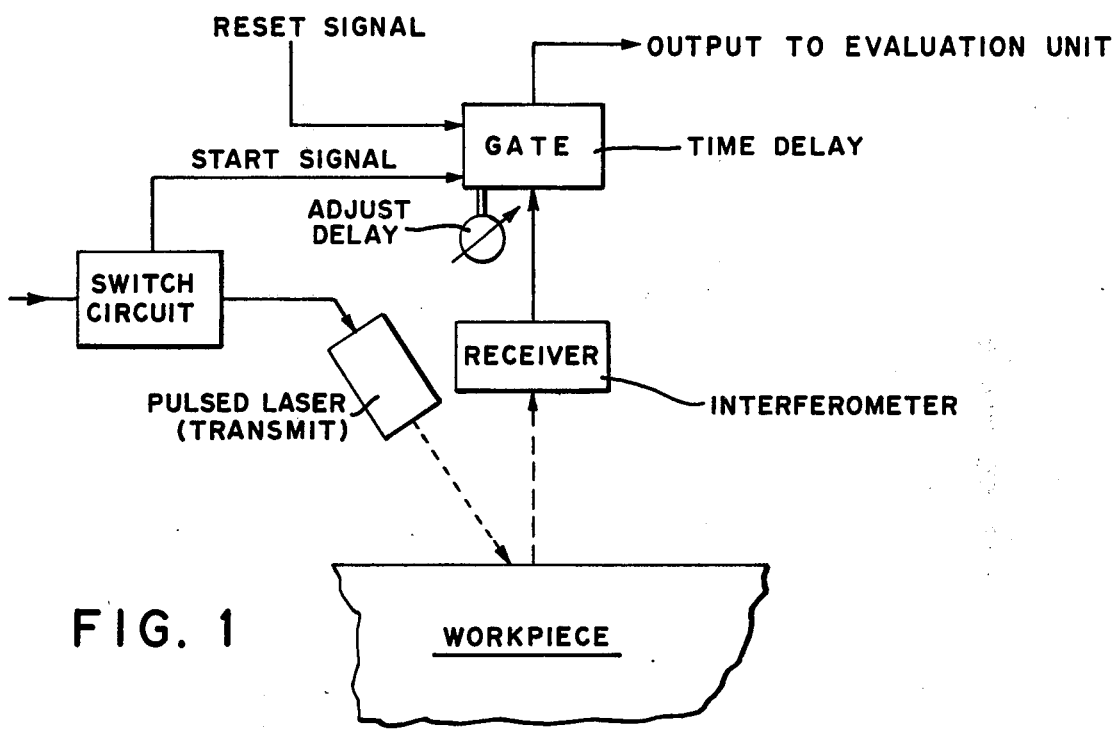
FIG. 1 is a schematic block diagram of a typical electrical control circuit of the invention.

Using the region of heaviest oxide layer, tests are made to reveal the quantity of laser beam pulses which must precede the laser beam pulse producing the same sound wave amplitude as had been obtained at the clean surface region of the workpiece. The adjustment so derived empirically, that is the determination of the quantity of laser pulses needed for cleaning the workpiece, can be maintained constant for a particular workpiece. Of course, for each laser beam pulse, including those used for cleaning, there is produced a respective acoustic wave. Only the sonic wave produced responsive to the last-transmitted laser beam pulse is used for test purposes. Such condition can be met in several ways. The pulse repetition rate of the laser source is known and, hence, the time delay from the initial laser pulse to the first laser beam pulse useable for acoustic exploration of the workpiece is programmable. By providing a time delay gate in the electrical output of the interferometer as seen in FIG. 1, the initial outputs arising from the laser pulses and used for cleaning are suppressed. Only after the passage of a delay, the time interval between the start signal and the end of a preset adjustable time delay, are the output signals permitted to pass to an evaluation unit.

Figure 2:
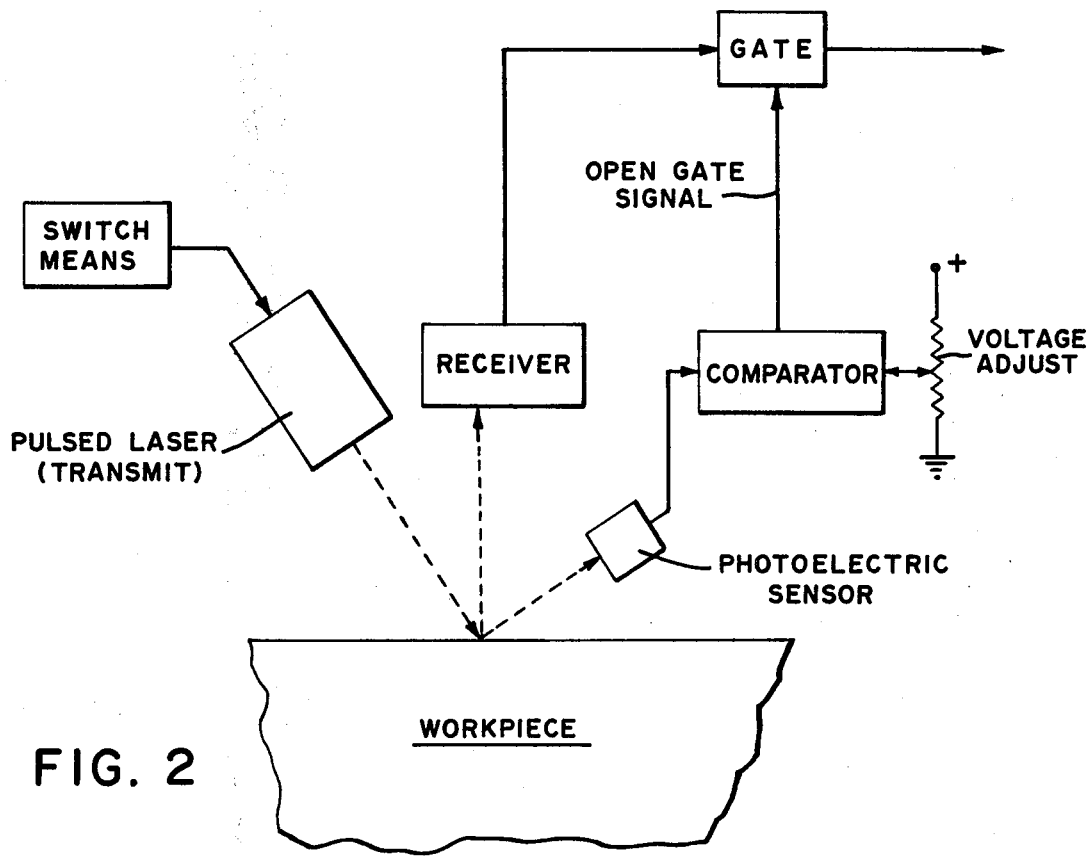
FIG. 2 is a schematic block diagram showing an alternative embodiment.

In another embodiment, instead of setting the delay for a predetermined constant quantity of laser beam pulses used for cleaning the surface of the workpiece, photoelectric means are used for determining the surface condition of the workpiece. The cleaning process performed by means of laser beam pulses is terminated when the output signal from the photoelectric means corresponds to a value corresponding to that obtained from a clean metal surface, see FIG. 2. In another embodiment, a circuit can be provided for sensing at the photoelectric means the condition when the reflected light responsive to two consecutive transmitted laser beam pulses remains constant, and thereafter a release signal is sent to the receiver for providing the acoustic wave responsive signal to the evaluation circuit.

It will be apparent that the invention is not limited to the use of a single laser source. For example, several laser sources can be used in such a manner that one laser source serves for cleaning the surface of the workpiece and another source for producing the acoustic wave. In the latter case, a sequencing circuit first operates the cleaning laser and subsequently activates the second laser used for producing the acoustic wave. Concurrently with rendering the second laser source operative the sequencing circuit also opens a gate circuit associated with the receiver means for permitting the acoustic wave responsive output signal derived from the deflection of the workpiece surface to pass to an evaluation circuit.

Moreover as used heretofore, the term "laser source" or equivalent expression shall be interpreted as including also a combination of laser beam sources.

What is claimed is:

1. Method for testing a workpiece by the acoustic wave test method using pulsed laser beam energy for producing an acoustic wave in the workpiece comprising:
   transmitting to the workpiece surface portion at which an acoustic wave is to be produced a plurality of laser beam pulses for removing contamination present at said workpiece surface portion;
   transmitting thereafter at least one further laser beam pulse to the same portion, the resulting acoustic wave propagated in the workpiece being used for nondestructively testing such workpiece;
   sensing the acoustic wave responsive to said further laser beam pulse after it has traversed a certain region of the workpiece, and
   evaluating said sensed acoustic wave.

2. Method for testing a workpiece by the acoustic wave test method as set forth in claim 1, said plurality of laser beam pulses for removing surface contamination being a constant quantity for a particular workpiece and a given surface contamination.

3. Method for producing by the thermal effect responsive to transmitting pulsed laser beam energy an acoustic wave in a workpiece for nondestructively testing such workpiece comprising the steps:
   transmitting to the workpiece surface portion at which an acoustic wave is to be produced laser beam pulses adapted for removing contamination present at said workpiece surface portion;
   sensing the condition when a normalized substantially contaminant-free surface condition has been achieved, and
   utilizing, responsive to sensing said normalized condition, the acoustic wave produced by the subsequent laser beam pulse for nondestructively testing the workpiece.

4. Method for producing by the thermal effect responsive to transmitting pulsed laser beam energy an acoustic wave in a workpiece for nondestructively testing such workpiece comprising the steps:
   transmitting to the workpiece surface portion at which an acoustic wave is to be produced laser beam pulses from a first laser source, such pulses being adapted for causing the removal of contamination present at said workpiece surface portion;
   subsequently transmitting to said surface portion at least one laser beam pulse from a second laser source, said latter pulse producing an acoustic wave in the workpiece propagating from said surface portion, and
   utilizing said acoustic wave responsive to the pulse from said second laser source for nondestructively testing the workpiece.

5. An apparatus for producing by the thermal effect responsive to transmitting pulsed laser beam energy an acoustic wave in a workpiece for nondestructively testing such workpiece comprising:
   laser means disposed for transmitting laser beam pulses to a surface portion of a workpiece, said pulses being adapted to cause removal of surface contamination and each pulse producing also a respective acoustic wave which is propagated in the workpiece from such portion;
   receiving means disposed for sensing the wave propagated in the workpiece from said portion after said wave has traversed a certain region of the workpiece, and
   control means coupled for causing said receiving means to be nonresponsive to acoustic waves produced by initial laser beam pulses which are used for removal of surface contamination.

6. An apparatus for producing by the thermal effect responsive to transmitting pulsed laser beam energy an acoustic wave in a workpiece as set forth in claim 5, said laser means comprising a first laser source for providing beam pulses for contamination removal and a second source for providing beam pulses the resulting acoustic waves of which propagated in the workpiece are used for sensing and evaluation by said receiving means.

7. An apparatus for producing by the thermal effect responsive to transmitting pulsed laser beam energy an acoustic wave in a workpiece as set forth in claim 5, said control means including timing means for causing said receiving means to be nonresponsive for an initial period during which laser beam pulses are transmitted from said laser means.

8. An apparatus for producing by the thermal effect responsive to transmitting pulsed laser beam energy an acoustic wave in a workpiece as set forth in claim 5, said control means including sensing means for determining when said surface portion has been normalized in a substantially contaminant-free surface condition and in response to such condition rendering said receiving means responsive for sensing said wave.

9. An apparatus for producing by the thermal effect responsive to transmitting pulsed laser beam energy an acoustic wave in a workpiece as set forth in claim 8, said sensing means including photoelectric means disposed to be responsive to the laser beam energy reflected from said workpiece portion.

* * * * *